US009271611B2

(12) United States Patent
Stratmann

(10) Patent No.: US 9,271,611 B2
(45) Date of Patent: Mar. 1, 2016

(54) SYSTEMS FOR IMPROVING HAND HYGIENE

(75) Inventor: Greg Stratmann, San Francisco, CA (US)

(73) Assignee: Hand Hygiene Systems, San Jose, CA (US)

( * ) Notice: Subject to any disclaimer, the term of this patent is extended or adjusted under 35 U.S.C. 154(b) by 20 days.

(21) Appl. No.: 12/331,112

(22) Filed: Dec. 9, 2008

(65) Prior Publication Data

US 2009/0265990 A1 Oct. 29, 2009

Related U.S. Application Data

(63) Continuation-in-part of application No. 12/114,519, filed on May 2, 2008, now abandoned.

(60) Provisional application No. 61/047,281, filed on Apr. 23, 2008.

(51) Int. Cl.

| | |
|---|---|
| ***A61L 2/18*** | (2006.01) |
| ***A47K 5/12*** | (2006.01) |
| ***E05B 1/00*** | (2006.01) |
| ***E05F 15/70*** | (2015.01) |
| ***E05F 15/75*** | (2015.01) |

(52) U.S. Cl.

CPC ................. *A47K 5/12* (2013.01); *E05B 1/0069* (2013.01); *E05F 15/70* (2015.01); *E05F 15/75* (2015.01); *E05Y 2800/00* (2013.01); *E05Y 2800/426* (2013.01); *E05Y 2900/112* (2013.01); *Y10T 16/46* (2015.01)

(58) Field of Classification Search

CPC ........................................................ A61L 2/18
USPC .................................. 422/191-192; 700/283
See application file for complete search history.

(56) References Cited

U.S. PATENT DOCUMENTS

| | | | | |
|---|---|---|---|---|
| 4,562,664 | A * | 1/1986 | Kambic | 49/14 |
| 4,620,502 | A * | 11/1986 | Kimble | 118/419 |
| 4,896,144 | A | 1/1990 | Bogstad | |
| 5,687,507 | A * | 11/1997 | Beran | 49/340 |
| 2002/0175182 | A1* | 11/2002 | Matthews | 222/52 |
| 2003/0008791 | A1 | 1/2003 | Chiang | |
| 2006/0121098 | A1 | 6/2006 | Mendoza et al. | |
| 2006/0289558 | A1 | 12/2006 | Parker | |
| 2007/0213877 | A1* | 9/2007 | Hart et al. | 700/282 |
| 2007/0216267 | A1* | 9/2007 | Johanning | 312/294 |
| 2007/0256362 | A1* | 11/2007 | Hansen | 49/32 |
| 2008/0087719 | A1 | 4/2008 | Sahud | |

OTHER PUBLICATIONS

Center for Disease Control and Prevention, "Guideline for Hand Hygience in Health-Care Settings," Morbidty and Mortality Weekly Report; Oct. 25, 2002; vol. 51, pp. 1-45.*
International Search Report for International Application PCT/US08/05443 mailed on Jul. 22, 2008.

(Continued)

*Primary Examiner* — Sean E Conley
*Assistant Examiner* — Donald Spamer
(74) *Attorney, Agent, or Firm* — Steptoe & Johnson LLP

(57) ABSTRACT

The invention relates generally to the field of hand sanitation, and particularly to a systems that encourage or compel the use of a hand sanitizer in order to open or unlock a door, unlock an access panel or drawer, or use a shared electronic device.

16 Claims, 6 Drawing Sheets

(56) References Cited

OTHER PUBLICATIONS

International Preliminary Report on Patentability for International Application PCT/US08/05443 issued on Oct. 26, 2010.

International Search Report for International Application PCT/US08/13519 mailed on Jan. 29, 2009.

International Preliminary Report on Patentability for International Application PCT/US08/13519 issued on Oct. 26, 2010.

* cited by examiner

INFECTION CONTROL WIRELESS INTERLOCKING SYSTEM BLOCK DIAGRAM

SYSTEMS FOR IMPROVING HAND HYGIENE

CROSS-REFERENCE TO RELATED APPLICATIONS

This application is a continuation-in-part of, and claims priority from, U.S. patent application Ser. No. 12/114,519, filed May 2, 2008, which claims the benefit of the filing date of U.S. provisional patent application 61/047,281, filed Apr. 23, 2008, each hereby incorporated by reference.

FIELD OF THE INVENTION

The invention relates generally to the field of hand sanitation, and particularly to a systems that encourage or compel the use of a hand sanitizer in order to open or unlock a door, unlock an access panel or drawer, or use a shared electronic device.

BACKGROUND OF THE INVENTION

Despite training, health-care, food, and transportation workers are poorly compliant with practices known to reduce the spread of infectious microbes, such as hand hygiene measures. For example, even the most vigorous attempts of infection control departments to increase health-care worker (e.g., nurses, physicians, and technicians) compliance with hand hygiene is limited to a sustained compliance rate of only 40%.

Health-care-associated infections are a common cause of morbidity and mortality in the United States and are among the most common adverse events in health-care. Infectious microbes that can be acquired or transmitted in a healthcare setting include: *Acinetobacter baumannii; Burkholderia cepacia;* chickenpox (varicella); *Clostridium difficile; Clostridium sordellii;* Creutzfeldt-Jakob Disease (CJD); ebola virus (viral Hemorrhagic Fever); hepatitis viruses A and B; influenzaviruses; MRSA (methicillin-resistant *Staphylococcus aureus*); mumps; norovirus; *streptococcal* species; *Pseudomonas Aeruginosa;* parvovirus; poliovirus; pneumonia; rubella; SARS; *S. pneumoniae;* tuberculosis; VISA (vancomycin intermediate *Staphylococcus aureus*); and VRE (vancomycin-resistant enterococci).

Poor compliance with hand hygiene protocols in the food service (e.g., food poisoning) and transportation (e.g., airplanes, cruise ships, and trains) industries also results in significant morbidity and mortality.

New systems designed to encourage hand sanitation are needed to reduce the spread of infectious microbes in these and other public and private settings.

SUMMARY OF THE INVENTION

In a first aspect, the invention features a door opening system that includes a hand sanitizer dispensing unit that releases a hand sanitizer upon activation, a door with a door opening device, an electrical, mechanical, or wireless signal connection between the hand sanitizer dispensing unit and the door opening device, and a manual override device, wherein the hand sanitizer dispensing unit transmits an activation signal to the door opening device upon activation, wherein the door opening device opens the door upon receipt of the activation signal, and wherein use of the manual override device allows bidirectional movement of the door independent of the activation of said hand sanitizer dispensing unit. The door opening system can further include a locking device that prevents movement of the door in the absence of an activation signal, wherein the locking device unlocks upon receipt of an activation signal.

In one embodiment of the first aspect of the invention, the hand sanitizer is a chemical or radiological sanitizer. Chemical sanitizers include triclosan, ethanol, isopropanol, n-propanol, povidone-iodide, chlorhexidine gluconate, octenidine, chloroxylenol, hexachlorophene, alkyl benzalkonium chloride, benzethonium chloride, cetrimide, and cetylpyridium chloride. In preferred embodiments, the chemical sanitizer is ethanol or chlorhexidine. The chemical hand sanitizer can be applied with a towel, towelette, or hand wipe. The radiological sanitizer can be ultraviolet light. In another embodiment, the hand sanitizer dispensing unit dispenses an emollient instead of a hand sanitizer at random or prescribed intervals.

In other embodiments of the first aspect of the invention, the door opening device is an automatic door opener. The manual override device can be a handle, knob, button, push pad, bar, or lever, or any device that allows movement of the door in the absence of an activation signal. The door can be a single, double, revolving, sliding, overhead, or elevator door. The wireless signal connection can be a radio or infrared connection. The hand sanitizer dispensing unit can be mounted on the door. In one embodiment, the door is located in a hospital, medical facility, nursing home, school, daycare center, library, museum, public meeting or working space, retail store, grocery store, restaurant, cafeteria, kitchen, food production or processing facility, public transportation station, or public transit vehicle. When located in a hospital, the door can be located in a hospital emergency room (ER), intensive care unit (ICU), operating room (OR), surgical preparation room, patient room, outpatient facility, birthing room, pharmacy, cafeteria, restroom, elevator bank, or waiting room. In another embodiment, the door is located in an airport, train station, subway station, or bus station, or in a mode of transportation such as an airplane, train, subway train, bus, or boat, such as a passenger cruise ship. In a further embodiment, the system includes instructions for the use of the hand sanitizer dispensing unit, door opening device, manual override device, or locking device.

In a second aspect, the invention features an access system for reducing the spread of infectious microbes that includes a hand sanitizer dispensing unit that dispenses a hand sanitizer upon activation, an enclosed storage area that has an access door, panel, or drawer, a locking device, and an electrical, mechanical, or wireless signal connection between the hand sanitizer dispensing unit and the locking device, wherein the hand sanitizer dispensing unit transmits an activation signal to the locking device upon activation, wherein the locking device prevents movement of the access door, panel, or drawer in the absence of the activation signal, and wherein the locking device unlocks upon receipt of the activation signal. The access door or panel can be located on a cabinet, closet, locker, or cart, such as those used to store medical supplies or medicaments.

In a third aspect, the invention features a shared electronic device system for reducing the spread of infectious microbes that includes a hand sanitizer dispensing unit that dispenses a hand sanitizer upon activation, a shared electronic device, and an electrical, mechanical, or wireless signal connection between the hand sanitizer dispensing unit and the shared electronic device, wherein the hand sanitizer dispensing unit transmits an activation signal to the shared electronic device upon activation, and wherein the shared communication electronic device is rendered operable upon receipt of the activation signal. In one embodiment, the shared electronic device is a computer, telephone, copying machine, fax machine, or scanner. In another embodiment, the shared electronic device is a public telephone. In a further embodiment, the system further includes a manual override device that allows use of the shared electronic device independent of activation of the hand sanitizer dispensing unit. Manual override devices suitable for use in a shared electronic device system include biometric readers, alphanumeric keyboards, computer mice, and identification card readers.

DEFINITIONS

By "door" is meant a moveable barrier meant to separate two distinct spaces within a structure. The door can be a single, double, sliding (vertical or horizontal), or revolving door. The door can be opened manually or automatically by a door opening device, as defined herein. Elevator doors and other doors found in the interior or exterior of modes of transportation are also suitable doors for use in the present invention. The door can be located in a stationary structure (e.g., a hospital, airport) or in a moving transport object (e.g., a train, boat, or airplane). The door can separate two public or private spaces or separate a public space from a private space (e.g., a door between a hospital hallway and a patient room). A door can also be an access panel or drawer, such as those found in closets, cabinets (e.g., supply or storage cabinets), tables, or desks.

By "effective amount" is meant the measured quantity of a chemical or radiological hand sanitizer that is necessary to reduce (e.g., by 5%, 10%, 20%, 30%, 40%, 50%, 60%, 70%, 80%, 90%, 95%, or 99%) or eliminate infectious microbes or pathogens from the skin surface of the hands, wrists, or forearms.

By "hand sanitizer" or "sanitizer" is meant any compound or means used to remove, reduce, or kill microbes and pathogens (e.g., bacteria, fungi, parasites, and viruses) upon application to the hands or lower arms of a human (e.g., a healthcare professional) that does not require removal following use, as required with standard hand-washing with soap and water. Hand sanitizers can be chemically or radiologically-based. A chemical sanitizer can be in a liquid, gel, foam, or powder form. Alternatively, a chemical sanitizer can be present on or within a towel (e.g., a towelette) or napkin. Active ingredients in a chemical hand sanitizer include but are not limited to: triclosan, ethanol (e.g., 62% w/w ethanol, such as PURELL®), isopropanol, n-propanol, povidone-iodide, chlorhexidine gluconate, octenidine, chloroxylenol, hexachlorophene, alkyl benzalkonium chloride, benzethonium chloride, cetrimide, and cetylpyridium chloride. Chemical hand sanitizers are discussed in further detail in the Center for Disease Control and Prevention's Morbidity and Mortality Weekly Report entitled "Guideline for Hand Hygiene in Health-Care Settings" (Vol. 51, Oct. 25, 2002). Chemical hand sanitizers can include other agents, such as emollients (e.g., moisturizing crèmes, lotions, and salves), chemical stabilizers, or dyes, that alter the sanitizer's chemical, physical, or biological (e.g., therapeutic) properties. A radiological-based hand sanitizer is a device that, upon activation, exposes a user's hands or lower arms to radiation (e.g., ultraviolet light) that is germicidal but not harmful to the user. See, e.g., U.S. Pat. No. 6,254,625, incorporated herein by reference.

DETAILED DESCRIPTION OF THE INVENTION

Figure 1:
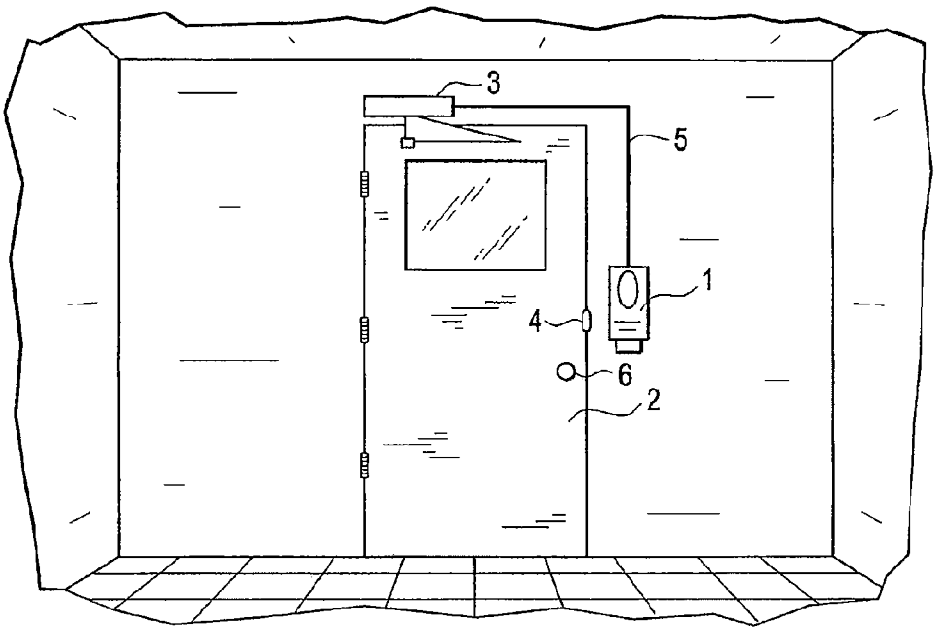
FIG. 1 is a perspective view of the door opening system of the invention in the context of a single door threshold.
Figure 2:
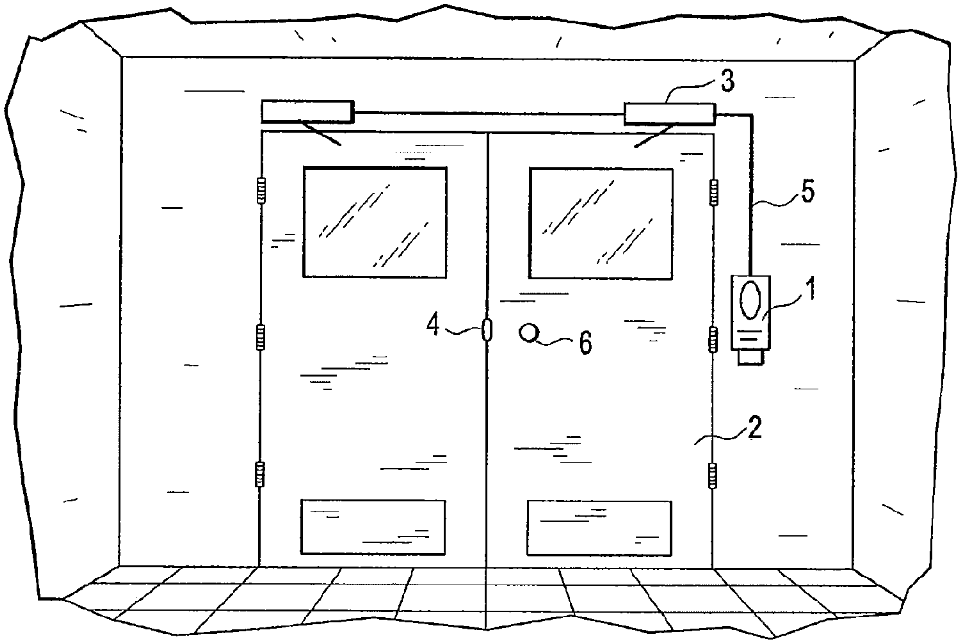
FIG. 2 is a perspective view of the door opening system of the invention in the context of a double door threshold.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The invention features systems that reduce the spread of infectious microbes by facilitating and rewarding the use of a hand sanitizer dispensing unit. By rewarding the use of a hand sanitizer, the systems of the invention will increase compliance with hygiene protocols and reduce the spread of infectious microbes. Each system of the invention, when activated, transmits a signal that allows the user to gain access to a defined space or the ability to use a shared electronic device. In some embodiments of the invention, use (i.e., activation) of a hand sanitizer dispensing unit is compelled in order to access a defined area (e.g., a building, room, hallway, closet, cabinet, or drawer) or to use a shared electronic device (e.g., a computer or telephone). The systems of the invention provide for the optional or enforced use of a hand sanitizer dispensing unit to gain access to a defined area or the use of a shared electronic device, thereby increasing the convenience or necessity of applying a hand sanitizer. Thus, the systems of the invention can improve hand hygiene and reduce the spread of infectious microbes by creating a path of least resistance that encourages the use of hand sanitizers.

Door Opening System

The door opening system of the invention allows for the convenient access to a defined or restricted space, such as a building, room (e.g., a restroom), hallway, or closet (e.g., a supply closet), by operably linking the use of a hand sanitizer dispensing unit with an door opening device (e.g., an automatic door opener). For example, the use of a hand sanitizer dispensing unit mounted near a doorway activates an automatic door opener, thereby allowing the user to quickly and easily pass through the door threshold without having to manipulate a door knob or latch. In one embodiment of the invention, the door is locked, and activation of the hand sanitizer dispensing unit unlocks and opens the door. Alternatively, activation of the hand sanitizer dispensing unit allows for the user to unlock the door by conventional means, for example, by exposing or activating a password, keycode, keycard, or biometric terminal or allowing the use of a physical key.

A door opening system of the invention includes a hand sanitizer dispensing unit, a door opening device, an electrical, mechanical, or wireless signal connection between the hand sanitizer dispensing unit and the door opening device, and a manual override device. In some embodiments of the invention, the system further incorporates a locking device that prevents the door from opening unless the hand sanitizer dispensing unit is activated or the manual override device is utilized. Each of these components is discussed in further detail below.

Exemplary door opening systems constructed in accordance with the present invention are shown in FIGS. 1-4. The door opening system includes a hand sanitizer dispensing unit, a door with a door opening device, an electrical, mechanical, or wireless signal connection between the dispensing unit and the door opening device, and a manual override device. Any person (i.e., a "user") desiring entry into a space blocked by a closed door can activate the door opening device by using the hand sanitizer dispensing unit to receive a quantity of a hand sanitizer. Use of the dispensing unit initiates two events: 1) the unit dispensation of an effective amount of a chemical or radiological hand sanitizer on to one or both hands of the user and 2) transmission of a signal from the dispensing unit that opens the door to allow the user entry past the threshold. Alternatively, a user who prefers or cannot activate the hand sanitizer dispensing unit (e.g., in an emergency situation) can still open the door by using a manual override device, as defined herein, attached to the door. Accordingly, use of the door opening system of the invention rewards the application of a hand sanitizer with the convenience of a door opening device, such as an automatic door opener.

Access System

The invention also features an access system that encourages or compels the use of a hand sanitizer dispensing unit to gain access to a locked storage area, such as a cabinet, closet, or drawer. Activation of a hand sanitizer dispensing unit sends a signal to a locking device that unlocks an access door, panel, or drawer to allow the user access to the protected area. The access system of the invention is particularly well suited for use in health-care environments for the storage of strictly controlled substances, such as anesthetics and narcotics. Medical storage carts and cabinets used by health-care workers to securely store or transport drugs and medicines in a health-care environment (e.g., a hospital) can incorporate a restricted access system of the method to reduce the spread of infectious microbes by health-care workers to patients.

Figure 5:
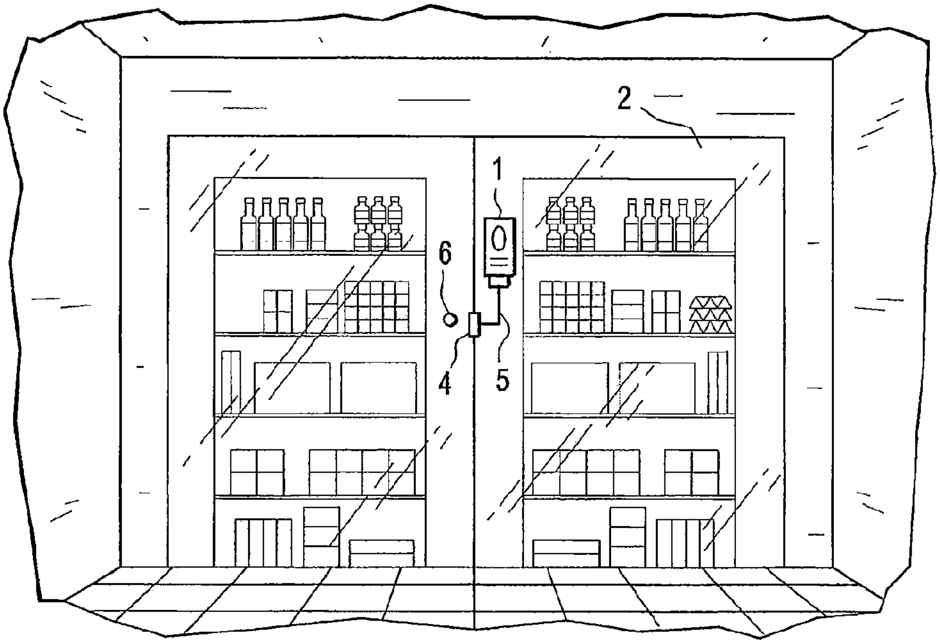
FIG. 5 is a perspective view of the access system of the invention in the context of a medical supply cabinet.

An access system of the invention includes a hand sanitizer dispensing unit, a locking device, and an electrical, mechanical, or wireless signal connection between the hand sanitizer dispensing unit and the locking device. Each of these components is discussed in further detail below. An exemplary access system of the invention is illustrated in FIG. 5.

The access system of the invention features a hand sanitizer dispensing unit that is used to gain access to a defined space that is protected by a locked access door, panel, or drawer. In this case, use of the hand sanitizer dispensing unit is required to unlock the access door, panel or drawer in order to gain access to the defined space. Alternatively, use of the hand sanitizer dispensing unit is not required to gain entry to the protected space, but rather serves as a convenient method of accessing the space. In this embodiment, the user can select from other methods of unlocking the access door, panel, or drawer apart from using the hand sanitizer dispensing unit. These other methods include, but are not limited to, the use of a key, keycard, passcard (e.g., identification card), biometric reading, password, or key code. In this embodiment, the convenience of using the hand sanitizer dispensing unit to open the access door, panel, or drawer will encourage the use of a hand sanitizer over the relative inconvenience of opening the door, panel, or drawer by conventional methods. Furthermore, the access system of the invention can also unlock an access door, panel, or drawer by conventional methods (e.g., key, keycard, passcard (e.g., identification card), biometric reading, password, or key code) when used in combination with a hand sanitizer dispensing unit. In this case, the use of the hand sanitizer dispensing unit does not alone unlock the access door, panel, or drawer, but enables the user to complete an additional unlocking step or steps, either before or after using the hand sanitizer dispensing unit, that grants the user access to the protected space.

The cabinet, closet, or drawer protected by a restricted access system of the invention can be located in a fixed position (e.g., a storage cabinet or desk) or can be mobile (e.g., a supply cart). For example, medical storage carts and cabinets can incorporate locking devices that require the user (e.g., a physician, nurse, or technician) to first activate a hand sanitizer dispensing unit and then enter a passcode, keycode, or swipe a keycard in order to access the contents of the cart or cabinet.

In one embodiment, use of the hand sanitizer dispensing unit does not initially unlock the locking device, but rather resets a programmable relocking interval. For example, in order to prevent unauthorized access, some locking devices can have programmable relocking intervals that require the user to unlock the cart or cabinet frequently (e.g., every 15 minutes). To encourage the frequent use of a hand sanitizer, a locking device with a programmable relocking interval can be used in a restricted access system of the invention. Once the user has unlocked the locking device, he or she must activate operably linked hand sanitizer dispensing unit to reset the programmable locking interval and prevent the access door, panel, or drawer from re-locking. Alternatively, use of the hand sanitizer dispensing unit increases the relocking interval, for example, by 5 minutes, 10 minutes, 15 minutes, 20 minutes, 30 minutes, 60 minutes, 120 minutes, or longer. In this case, the user, having activated the hand sanitizer dispensing unit and applied a hand sanitizer, is rewarded with the convenience of temporary access to the protected space without the periodic requirement of unlocking the access, door, or panel. Thus, activation of the hand sanitizer dispensing unit rewards the user with convenience without requiring the user to continuously unlock the locking device by conventional methods.

Shared Electronic Device System

The invention further features a shared electronic device system that reduces the spread of infectious microbes by regulating the use of communally used electronic devices, such as computers, telephones, copying machines, fax machines, and scanners. Shared electronic devices are especially prevalent in health-care settings (e.g., hospitals, clinics, and nursing homes), the use of which facilitates the fast and pervasive spread of infectious microbes amongst health-care workers (e.g., nurses, physicians, and technicians) and their patients.

Figure 6:
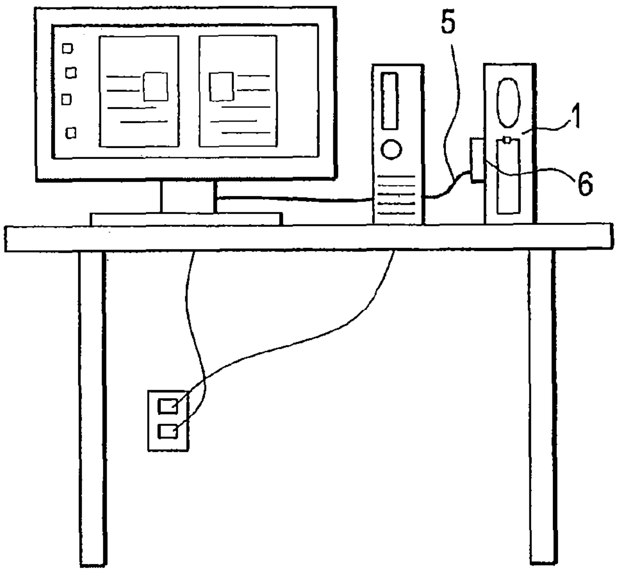
FIG. 6 is a perspective view of the shared electronic device system of the invention in the context of a computer.

A shared electronic device system of the invention includes a hand sanitizer dispensing unit, a shared electronic device, and an electrical, mechanical, or wireless signal connection between the hand sanitizer dispensing unit and the shared electronic device. Each of these components is discussed in further detail below. An exemplary shared electronic device system of the invention is illustrated in FIG. 6.

The shared electronic device system of the invention regulates the use of a shared electronic device by allowing the use of a device that is otherwise (i.e., by default) inactivated or rendered inoperable when the user activates a hand sanitizer dispensing unit that is operably linked to the device. Accordingly, use of the shared electronic device is restricted to users that have sanitized their hands by using the hand sanitizer dispensing unit. For example, a computer that is connected to a shared electronic device system of the invention is inactivated or locked in its default state. Activation of the hand sanitizer dispensing unit activates the computer to allow subsequent use by the user.

Alternatively, the shared electronic device system of the invention can be configured to allow for the optional use of the hand sanitizer dispensing unit to activate the shared electronic device. In this embodiment, use of the hand sanitizer dispensing unit is represents a convenient method of unlocking the shared electronic device, but the device can be unlocked by other means, such as entering a code or password, swiping a passcard, or a supplying a biometric reading (e.g., fingerprint scan). A shared electronic device incorporated in such as system allows the user to choose In one embodiment, use of the hand sanitizer dispensing unit is required for the continued use of the shared electronic device for a duration of time. For example, the user must activate the hand sanitizer dispenser unit every 1, 2, 3, 4, 5, 6, 7, 8, 9, 10, 11, 12, 13, 14, 15, 20, 30, 45, 60 minutes or more in order to continue using the shared electronic device (i.e., to prevent the device from entering a inactive state). Thus, a shared electronic device system of the invention can include a programmable inactivation interval that requires the frequent application of a hand sanitizer. Therefore, activation of the hand sanitizer dispensing unit compels the user to use a hand sanitizer in order to continue using the shared electronic device.

Components

The individual components of the systems of the invention are described in further detail below and accordingly numbered in FIGS. 1-6.

1. Hand Sanitizer Dispensing Unit

A hand sanitizer dispensing unit is a device that, upon activation, dispenses, applies, or exposes a predetermined and effective amount of a hand sanitizer to the hands of a user. The hand sanitizer can be chemical (e.g., an alcohol-based sanitizer) or radiological (e.g., ultraviolet light), as defined herein.

A chemical hand sanitizer dispensing unit dispenses a measured quantity (e.g., 0.5 mL, 0.75 mL, 1.0 mL, 1.25 mL, 1.5 mL, 1.75 mL, 2.0 mL, 2.5 mL, 3.0 mL, 3.5 mL, 4.0 mL, 4.5 mL, 5.0 mL or more) of a chemical hand sanitizer that, when applied evenly over the surface of both hands, is effective in reducing or eliminating microbes. A chemical hand sanitizer dispensing unit consists of a structural or ornamental casing, a reservoir to hold a quantity of chemical hand sanitizer, a dispensing head or nozzle, and an activation trigger, such as a button, lever, or pull arm. Upon dispensation of a chemical hand sanitizer, the user rubs his or her hands together to evenly apply the sanitizer.

A hand sanitizer dispensing unit can also dispense a towel (e.g., a towelette or disposable hand wipe; see e.g., U.S. Pat. No. 4,620,502) containing or infused with a chemical hand sanitizer. The towel can be dispensed ready-to-use, or can be packaged (e.g., in foil wrapping) to preserve moisture content. Upon receipt of the towel, the user contacts it to his or her hands to apply the chemical hand sanitizer evenly over the surface of the skin.

A radiological hand sanitizer unit emits radiological energy (e.g., ultraviolet light) upon activation. Exposure of the users hands to this energy is effective in reducing or eliminating infectious microbes from the surface of the skin.

A hand sanitizer dispensing unit must be activated in order to release a hand sanitizer or sanitizing towel. A hand sanitizer dispensing unit is activated by the user by providing an affirmative stimulus to the unit. Stimuli include, e.g., pushing or pulling a lever or stepping upon or touching a pressure or weight-sensitive pad or button. Alternatively, a dispensing unit can be activated by sound (e.g., a voice or hand clap), proximity (e.g., optical (i.e., visible spectrum, magnet strips, ID cards), infrared, or thermal detection of user proximity), or motion (e.g., detection of a hand or finger close (e.g., 6 inches or less) to the dispensing unit).

A hand sanitizer dispensing unit can also dispense an emollient, such as a moisturizing crème, lotion, or salve, upon activation. Frequent use of chemical hand sanitizers can lead to uncomfortable, dry, or damaged skin, which serves to reduce compliance with hand hygiene protocols. The hand sanitizer dispensing units of the invention can dispense a therapeutic emollient at random or predetermined intervals, or upon express request by the user to mitigate the skin damage caused by chemical hand sanitizers. For example, the hand sanitizer dispensing unit can dispense an emollient instead of a hand sanitizer upon every 2nd, 3rd, 4th, 5th, 6th, 7th, 8th, 9th, 10th, or more activation of the hand sanitizer dispensing unit. Alternatively, a hand sanitizer dispensing unit that tracks and records the use of the hand sanitizer dispenser by individual users, as described herein, can be programmed to provide an emollient in lieu of a hand sanitizer according to a predetermined interval. The hand sanitizer dispensing unit can also allow for the express dispensation of an emollient by incorporating a dedicated button, lever, or other affirmative stimulus, as described above, that specifically controls release of the emollient. Allowing the user to select or have the chance of receiving an emollient upon activation of the hand sanitizer dispensing unit will encourage the use the systems of the invention by preventing skin damage caused by frequent application of chemical hand sanitizers.

A hand sanitizer dispensing unit can be mounted to a wall, door, table, desk, or cart. Alternatively, a dispensing unit can be free-standing (e.g., placed on a desk or table), suspended (e.g., from the ceiling), or supported by an integrated or attached stand. A hand sanitizer dispensing unit can be permanently mounted at a specified location, or can be configured for mobility (e.g., attachment to a mobile object, such as a push-cart).

The location of the hand sanitizer dispensing unit is important for efficient practice of the methods of the invention. For example, when incorporated into a door opening system of the invention, the dispensing unit is ideally located on or near the door to which it regulates passage. Instructional signs can be placed near the door or dispensing unit to advise a person unfamiliar with the door opening system of the invention (i.e., activating the dispensing unit to open the door) how to activate the dispensing unit in order to open or unlock the door. The hand sanitizer dispensing unit and additional instructions are preferably located to allow even a first-time user to quickly appreciate that the optional or required activation of the dispensing unit and receipt of a hand sanitizer allows passage through the door threshold.

A hand sanitizer dispensing unit can be operably linked, by way of a signal connection, as discussed herein, to more than one door, access panel, drawer, or shared electronic device. For example, a hand sanitizer can be operably linked to 1, 2, 3, 4, 5, 6, 7, 8, 9, 10, or more doors, access panels, drawers, or shared electronic devices. Conversely, a single door, access panel, drawer, or shared electronic device can be operably linked, by way of a signal connection, as discussed herein, to more than one hand sanitizer dispensing unit. For example, the use of a shared electronic device (e.g., a computer) can be controlled according to the usage of 1, 2, 3, 4, 5, 6, 7, 8, 9, 10, or more hand sanitizer dispensing units.

2. Doors, Access Panels, and Drawers

Any single, double, revolving, sliding (e.g., vertical or horizontal sliding doors), overhead, or elevator door can be incorporated into a door opening system of the invention. Doors, when in a closed position and restricting access, can be either locked or unlocked. With respect to an unlocked door, use of the door opening system of the invention causes a door opening device (as discussed below) to open the door upon receipt of a signal from the hand sanitizer dispensing unit. In this instance, the door opening device allows for the convenient passage of a user through a door threshold without the need to manually open the door. In addition, the door opening system of the invention can be applied to a locked door (i.e., a door further equipped with a locking device, as discussed below). In this case, activation of the door opening system, by triggering the dispensing unit as described above, is a requisite step the user must take to unlock the door.

Figure 3:
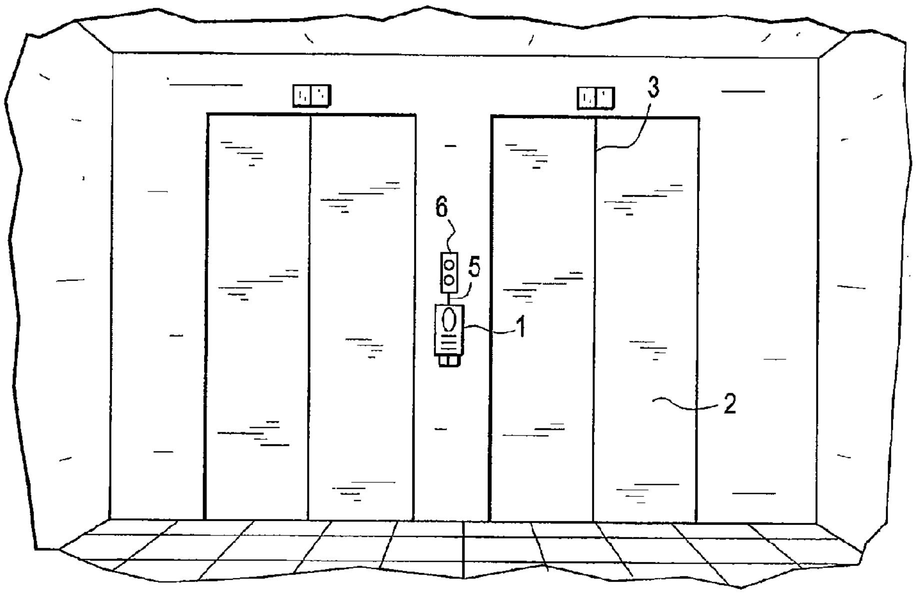
FIG. 3 is a perspective view of the door opening system of the invention in the context of an elevator door.
Figure 4:
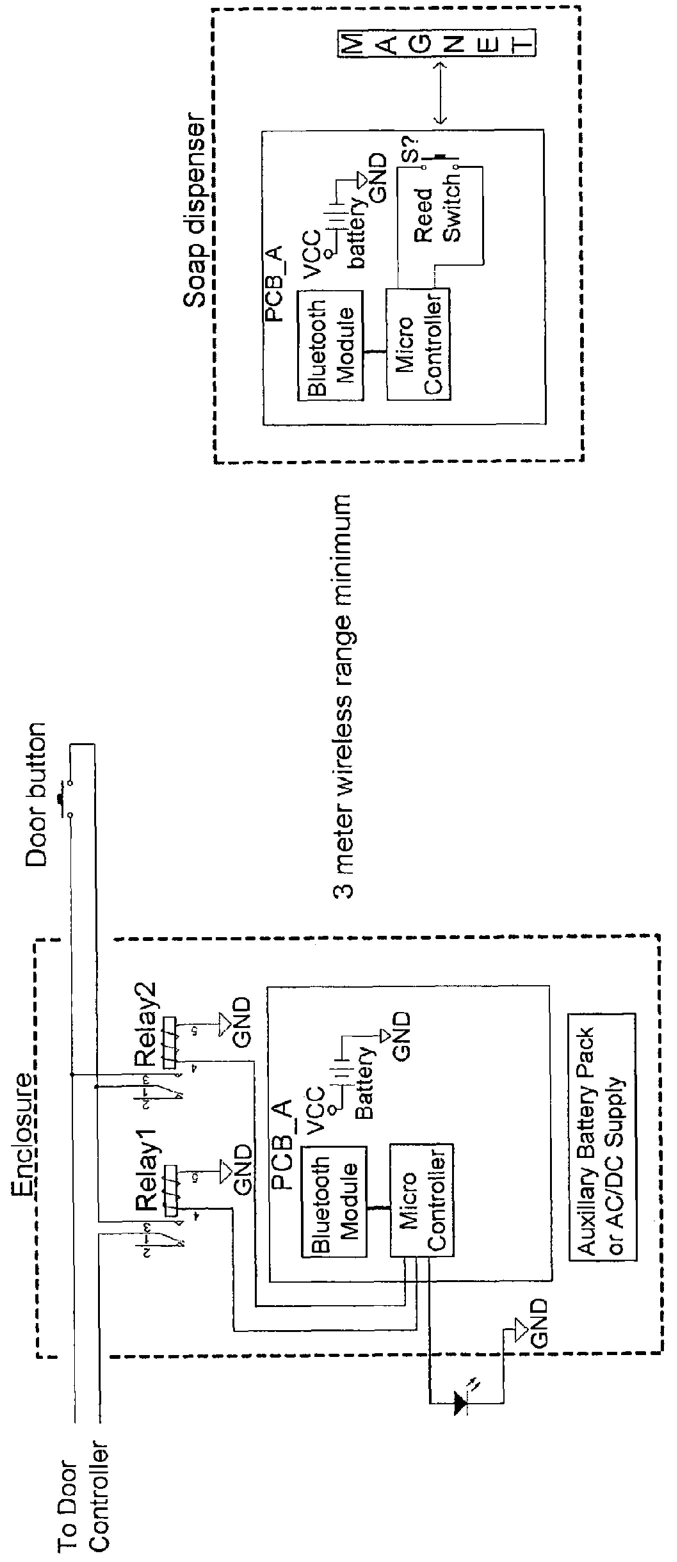
FIG. 4 is a block diagram of a door opening system of the invention that illustrates a wireless hand sanitizer dispensing unit and a receiver control unit operably connected to an automatic door opener.

Elevator doors can also be used in the door opening system of the invention, as illustrated in FIG. 3. Typically, elevators must be "called" by pressing a button located near the exterior door. When coupled to the system of the invention, activation of a hand sanitizer dispensing unit placed near an elevator door or bank can itself be used as an elevator call signal. Alternatively, the elevator call button remains in an inactive default state that only becomes functional upon the receipt of a signal from the hand sanitizer dispensing unit.

The access system of the invention features locking access doors, panels, or drawers. Such doors, panels, or drawers are commonly found in storage closets, cabinets, carts, and desks.

3. A Door Opening Device

A door opening device of the invention is a mechanical device that opens one or more doors upon receipt of a signal from a hand sanitizer dispensing unit. The device can use a motor, engine, or hydraulic arm to effect the movement of the door. Door opening devices (e.g., mechanical devices, such as hydraulic door openers) are known in the art (e.g., U.S. Pat. Nos. 2,591,693, 3,708,915, 4,660,324, and 4,348,835, herein incorporated by reference). Door opening devices, are colloquially known as "automatic door openers" and are frequently encountered when entering supermarkets and other retail spaces. Door opening devices can include a power supply (e.g., an electrical current) if necessary for operation.

4. A Locking Device

In one embodiment of the invention, the door opening system regulates access to a controlled area by including a locking device. In this case, the use of hand sanitizer dispensing unit is necessary in order to open the door. For example, use of the hand sanitizer dispensing unit can allow for the subsequent entry of a personal credential (e.g., password, keycode, or biometric reading) or physical key (e.g., a key or keycard) that, in combination, activates the door opening device and opens the door.

Locking devices (e.g., a door lock) of the invention can be based on a mechanical, electrical, or magnetic designs and serve to prevent the movement of a door, panel, or drawer when in a closed and locked position. Locking devices suitable for inclusion in the system of the invention are known to skilled artisans that install and maintain doors, panels, and drawers. Locking devices can include a power supply (e.g., an electrical current) if necessary for operation.

5. A Signal Connection Between the Dispenser Unit and Door Opening or Locking Device Upon activation, the hand sanitizer dispensing unit of the invention transmits a signal, through a signal connection, to the door opening device, locking device, or shared electronic device, as discussed herein. The signal connection can be wired (e.g., copper electrical wires that physically connect the dispensing unit to the door opening or locking device) to allow the transmission of an electrical signal. Alternatively, the signal connection can be wireless connection. Wireless connections include infrared and radio (e.g., Bluetooth, WiFi/802.11, ZigBee, WiMax, universal mobile telecommunications system (UMTS), general packet radio service (GPRS), code division multiple access 2000 (CDMA2000), global system for mobile communication (GSM), cellular digital packet data (CDPD), high-speed downlink packet access (HSDPA), or third generation (3G) protocol) signals. In this case, the dispensing unit contains a wireless transmitter that emits a signal upon activation of the unit. Upon receipt of a signal through the signal connection, the door opening device, locking device, or shared electronic device is activated or unlocked, allowing the user access past a door, panel, or drawer, or allowing the use of the shared electronic device.

6. A Manual Override Device

The door opening and shared electronic device systems of the invention can include a manual override device that allows the user to open or unlock a door, panel, or drawer without first activating a hand sanitizer dispensing unit, as discussed above. Thus, the manual override device acts as a fail-safe mechanism that allow the user to bypass the system of the invention (e.g., activating a hand sanitizer dispenser unit) in the event of mechanical or electrical failure (e.g., loss of electrical power). For example, a user that has an allergy to a chemical hand sanitizer can utilize the manual override device to open a door incorporated into a door opening system of the invention, thereby bypassing the need to activate the hand sanitizer dispensing unit.

Manual override devices of the invention can be electrical or mechanical in operation. A manual override device attached to an unlocked door can be a door handle, knob, push plate, pull bar, or any other means of opening a door that doesn't require the user to activate a hand sanitizer dispensing unit. In the case of a locked door, a manual override device negates the necessity to activate the hand sanitizer dispensing unit, but the user must still unlock the door by conventional means. When incorporated into a shared electronic device system of the invention, a manual override device allows the user to bypass the requirement of activating the hand sanitizer dispenser unit prior to or during the use of the shared electronic device. For example, the use could enter a code displayed on the computer or telephone screen to bypass the system of the invention. Alternatively, the user could use a biometric reader, alphanumeric keyboard, computer mouse, or identification card reader to bypass the system of the invention and activate the shared electronic device.

In any embodiment of the invention, the manual override device can be a switch, button, lever, or other means to inactivate the system of the invention. For example, the hand sanitizer dispensing unit can incorporate a button that says "override" or "bypass" that a user can optionally press in lieu of activating the hand sanitizer dispensing unit.

Advantages

The systems of the invention can encourage or compel a person at risk of transmitting or becoming infected with a microbial pathogen to apply an effective amount of hand sanitizer to their hands before passing through a doorway, opening a cabinet or drawer, or using a shared electronic device (e.g., a telephone or computer). Traditionally, in health-care (e.g., hospitals), food preparation and service (e.g., kitchens), and public transportation (e.g., cruise ships, airports) settings, hand-washing is encouraged to limit the transmission of microbial infections. Stand-alone hand sanitizer dispensing units are also frequently placed in health-care settings to reduce the spread of infectious microbes. In the absence of compulsion (e.g., employee surveillance or hand-washing "checklists") or reward (e.g., convenience), many individuals do not properly disinfect their hands, either by hand-washing or by using a hand sanitizer, frequently enough to reduce the transmission of infectious microbes. The systems of the present invention provide a convenient method to reduce or eliminate the transmission of infectious microbes amongst humans. The application of the system of the invention to several settings is considered below:

Health-Care Facilities

The systems of the invention can be ideally used in locations where it is extremely important to control the spread of microbes and pathogens that cause health-care-associated infections. As discussed, hospitals and other health-care facilities (e.g., nursing homes, outpatient clinics, and blood-donation centers) suffer from high transmission rates of microbial infections, greatly increasing the morbidity and mortality of those receiving medical treatment at these facilities. Doors that separate patient areas (e.g., patient rooms, surgical procedure rooms, and intensive care units) from common areas, such as hallways or waiting rooms, can be equipped with the door opening system of the invention. The door opening system of the invention is particularly useful used to limit access to immuno-compromised medical patients (e.g., patients that have received ablative irradiation prior to transplantation or patients suffering from acquired immunodeficiency syndrome (AIDS)).

Food Preparation

It is recognized that transmission of microbial pathogens from the hands to food products is a frequent means of communicating diseases, often responsible for severe illness or death. Numerous episodes involving fatalities due to contamination of food products during food handling have increased the public awareness of the serious consequences of poor hygiene in food preparation, distribution, or consumption settings. Although proper hand-washing hygiene is typically stressed, the reality is often poor compliance by the food preparers, handlers, cooks, and servers. Food preparation and service facilities such as slaughterhouses; food (e.g., meat, poultry, vegetable, fruit, or dairy products intended for human or other animal consumption) collection, processing, packing, and storage facilities; kitchens (e g., a home, school, hospital, or cafeteria kitchen); cafeterias; and restaurants are particularly vulnerable to harboring and transmitting microbial infections. In these settings, the use of the door opening system of the invention would encourage or compel food preparation and service personnel (e.g., butchers, harvesters, meat packers, cooks, and waiters) to apply a hand sanitizer to their hands prior to entering or exiting a food preparation area.

Transportation

Modes of transportation, especially public transportation vehicles and transportation stations (e.g., an airport), are frequent locations for the spread of infection microbes. The close proximity of many people, often in the absence of hand-washing facilities, makes these environments ideal for the transmission of disease-causing pathogens. Holiday cruise ships have been demonstrated to be especially vulnerable by the frequent and intense outbreaks of gastrointestinal infections, especially norovirus infections. The use of the door opening system of the invention throughout a cruise ship, airport, airplane, or train can reduce or eliminate the transmission of infectious microbes. For example, restroom doors could be equipped with the door opening system of the invention to encourage or compel anyone entering or exiting a restroom to apply a hand sanitizer.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A door opening system comprising:

a hand sanitizer dispensing unit that dispenses a hand sanitizer upon activation;

a door opening device;

a signal connection between the hand sanitizer dispensing unit and the door opening device; and a door that restricts passage through a threshold, the door including a manual override device that includes one of a knob, a handle, a push plate, and a pull bar and that can be operated by a user of the hand sanitizer dispensing unit to bypass the activation; and a locking device that prevents opening of the door, wherein the locking device locks the door after a first relocking interval expires, wherein the first relocking interval is programmable by the locking device, wherein a subsequent activation of the hand sanitizer dispensing unit causes the locking device to program the first relocking interval to a second relocking interval and lock the door after the second relocking interval expires, and wherein the second relocking interval is longer than the first relocking interval, wherein the hand sanitizer dispensing unit transmits an activation signal to the door opening device upon the activation, wherein the door opening device substantially opens the door upon receipt of the activation signal, wherein operation of the manual override device includes applying user motion to the door to substantially open the door independent of user activation of the hand sanitizer, wherein substantially opening the door allows the user to pass through the threshold, and wherein applying user motion includes one of turning a handle, turning a knob, pushing on a push plate, and pulling on a pull bar.

2. The door opening system of claim 1, wherein the locking device unlocks upon receipt of the activation signal or upon operation of said manual override device.

3. The system of claims 1, wherein the hand sanitizer comprises a chemical or radiological sanitizer.

4. The system of claim 3, wherein the chemical sanitizer is ethanol.

5. The system of claim 3, wherein the chemical sanitizer is chlorhexidine.

6. The system of claim 3, wherein the chemical hand sanitizer is applied with a towel, towelette, or hand wipe.

7. The system of claim 3, wherein the chemical hand sanitizer further comprises an emollient.

8. The system of claim 3, wherein the radiological sanitizer is ultraviolet light.

9. The system of claim 1, wherein the hand sanitizer dispensing unit dispenses an emollient instead of the hand sanitizer at random or prescribed intervals.

10. The system of claim 1, wherein the door opening device comprises an automatic door opener.

11. The system of claim 1, wherein the manual override device can be used to allow movement of the door in the absence of the activation signal.

12. The system of claim 1, wherein the signal connection comprises a radio or infrared connection.

13. The system of claim 1, wherein the door is a single, double, revolving, sliding, overhead, or elevator door.

14. The system of claim 1, wherein the hand sanitizer dispensing unit is mounted on the door.

15. The system of claim 2, further comprising instructions for the use of the hand sanitizer dispensing unit, door opening device, manual override device, or locking device.

16. A door opening system comprising:

a door that restricts passage through a threshold, the door including manually operated mechanism;

a door opening device;

a hand sanitizer dispensing unit that dispenses a hand sanitizer and transmits a signal to the door opening device upon user activation of the hand sanitizer; and a locking device that prevents opening of the door, wherein the locking device locks the door after a first relocking interval expires, wherein the first relocking interval is programmable by the locking device, wherein a subsequent activation of the hand sanitizer dispensing unit causes the locking device to program the first relocking interval to a second relocking interval and lock the door after the second relocking interval expires, and wherein the second relocking interval is longer than the first relocking interval;

wherein upon receiving the transmitted signal, the door opening device substantially opens the door independent of a user manipulating the manually operated mechanism, wherein upon a user manipulating the manually operated mechanism and one of pushing and pulling on the door, the door substantially opens independent of user activation of the hand sanitizer, and wherein substantially opening the door allows the user to pass through the threshold.

* * * * *